United States Patent
Zimmermann et al.

(10) Patent No.: US 8,451,138 B2
(45) Date of Patent: *May 28, 2013

(54) CRYOGENIC STORAGE DEVICE COMPRISING A TRANSPONDER

(75) Inventors: Heiko Zimmermann, St. Ingbert (DE); Guenter R. Fuhr, Berlin (DE); Rolf Hagedorn, Berlin (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/158,046

(22) Filed: Jun. 10, 2011

(65) Prior Publication Data

US 2011/0277486 A1    Nov. 17, 2011

Related U.S. Application Data

(63) Continuation of application No. 10/501,703, filed as application No. PCT/EP03/00615 on Jan. 22, 2003, now Pat. No. 7,958,791.

(30) Foreign Application Priority Data

Jan. 22, 2002    (DE) .................................. 102 02 304

(51) Int. Cl.
  *G01N 1/42*    (2006.01)
  *C12N 1/00*    (2006.01)
  *C12Q 3/00*    (2006.01)
  *G08C 17/04*    (2006.01)

(52) U.S. Cl.
  USPC ............... 340/870.31; 73/863.01; 73/863.11; 73/864.91; 435/3; 62/126

(58) Field of Classification Search
  None
  See application file for complete search history.

(56) References Cited

U.S. PATENT DOCUMENTS

| 4,652,827 A | * | 3/1987 | Eguchi et al. | 324/322 |
| 4,814,595 A | * | 3/1989 | Gilboa | 235/492 |
| 4,864,633 A | * | 9/1989 | Chatelot | 455/41.1 |
| 5,241,160 A | * | 8/1993 | Bashan et al. | 235/380 |
| 6,088,741 A | * | 7/2000 | Murata | 710/20 |

(Continued)

FOREIGN PATENT DOCUMENTS

| DE | 4418005 A1 | 11/1995 |
| DE | 19621179 A1 | 11/1997 |

(Continued)

OTHER PUBLICATIONS

Finkenzeller, K., "RFID Handbook Fundamentals and Applications in Contactless Smart Cards and Identification", ISBN 0470844027, original German publication by Hanser-Verlag, Munich, 2000, German Contents pp. VII-XIV.
International Search Report for PCT/EP03/00615 (May 30, 2003).

*Primary Examiner* — Thomas P Noland
(74) *Attorney, Agent, or Firm* — Caesar, Rivise, Bernstein, Cohen & Pokotilow, Ltd.

(57) ABSTRACT

A method for operating a cryostorage device (100), especially for biological samples, is described which comprises a sample carrier (10) to receive at least one sample (11) and a data storage (20), wherein data are inductively transmitted from the data storage device (20) into a wireless transmission channel (40) and/or conversely using a resonant circuit (30) connected to the data storage device (20).

9 Claims, 2 Drawing Sheets

U.S. PATENT DOCUMENTS

| | | | |
|---|---|---|---|
| 6,646,238 B1 * | 11/2003 | Fuhr et al. | 435/1.3 X |
| 6,677,857 B2 | 1/2004 | Bara et al. | |
| 6,931,864 B2 | 8/2005 | Fuhr et al. | |
| 2002/0023441 A1 * | 2/2002 | Bara et al. | 62/125 |
| 2003/0001574 A1 * | 1/2003 | Kroeckel et al. | 324/318 |
| 2004/0065093 A1 * | 4/2004 | Fuhr et al. | 435/1.3 X |
| 2004/0101966 A1 * | 5/2004 | Davis et al. | 436/43 |
| 2005/0247782 A1 * | 11/2005 | Ambartsoumian | 235/385 |
| 2006/0283197 A1 * | 12/2006 | Schon et al. | 62/173 |
| 2008/0104976 A1 | 5/2008 | Guglielmetti et al. | |
| 2009/0023128 A1 * | 1/2009 | Zimmermann et al. | 435/1.3 |

FOREIGN PATENT DOCUMENTS

| | | |
|---|---|---|
| DE | 10060889 A1 | 6/2002 |
| DE | 10144925 A1 | 3/2003 |
| EP | 0974798 A2 | 1/2000 |
| EP | 0974798 A3 | 1/2000 |
| GB | 2308947 A | 7/1997 |
| WO | 0033005 A1 | 6/2000 |
| WO | WO 0068663 A1 * | 11/2000 |

* cited by examiner

CRYOGENIC STORAGE DEVICE COMPRISING A TRANSPONDER

BACKGROUND

The invention relates to methods for operating a cryostorage device which is arranged for storage and/or preservation of biological samples especially, and especially methods for data transmission during cryostorage as well as cryostorage devices for implementing such methods.

Cryostorage is a generally known technique for the storage and/or preservation of samples having a temperature-sensitive lifetime or stability, such as biological samples for example. Depending on the specific task, animal or vegetable products, organs of living beings or parts of biological systems, such as cells, cell constituents, macromolecules, microorganisms, viruses or the like are transferred to a reduced-temperature state and stored. For preservation over long periods of time storage preferably takes place at liquid-nitrogen temperature or in a nitrogen-vapour atmosphere.

Patent Applications DE 100 60 889 and DE 101 44 925, which were unpublished at the foreign priority filing date of the present patent application, describe devices for the cryostorage of microscopically small biological samples. In these it is especially provided to deposit the samples in a cryostorage device each together with sample data which are characteristic to the relevant samples. There is a need to read or supplement the sample data in the data storages whilst the sample is in the cryopreserved state. Depending on the storage principle of the sample data, data-bus-bound or optical access to the data storage device has conventionally been realised. This may have the disadvantage that the handling capability of the cryostorage can be limited.

In data transmission technology transponder systems are increasingly replacing the conventional identification of objects using bar codes. Applications for example are known in automated production (automobile industry), monitoring technology (access control), in living animal identification or route tracking (e.g. courier services). Transponders having a wide range of designs matched to the particular application are known (for a review see K. Finkenzeller "RFID Handbook", Hanser-Verlag, Munich, 2000).

The term transponder as an abbreviation of "transmitter" and "responder" designates a transmitting and receiving device which shows a reaction, e.g., gives an answer to a received and evaluated enquiry. In general, a transponder comprises a resonant circuit and an integrated circuit with a data storage device (e.g. EEPROM). Data transmission from the data storage (transponder storage) via a wireless transmission channel e.g. to a central control system takes place by using the resonant circuit as a transmitting or receiving antenna. The resonant circuit is tuned to a certain transmitting or receiving frequency (e.g. 62 kHz). For power supply especially during the write/read process the transponder is exposed to an electromagnetic alternating field at a different frequency, e.g., twice the frequency (e.g. 124 kHz) with which a current is induced in the resonant circuit. Transponders typically have a range of around 80 cm. The circuit typically contains a voltage regulator, a frequency divider and an encoder.

Advantages of transponders consist in their miniaturisability and access security. For example, space-saving transponders in foil form (so-called smart labels such as the "Tag-it" transponders from Texas Instruments) are known. Authentification and encryption methods are known for implementing access security. One problem with transponder systems however is that their transmission function is sensitively dependent on the ambient conditions. For example, metallic materials and strong electromagnetic foreign fields in the vicinity can limit the range of transponders to around 20 cm. For this reason, the use of transponder systems has so far been limited to the afore-mentioned tasks with sufficiently well controllable ambient conditions.

The object of the invention is to provide an improved method with which the above disadvantages of conventional cryostorage methods are overcome and which have a simplified handling capability and an extended range of application. Methods according to the invention should especially make it possible to achieve fast and secure access to sample data regardless of the operating state of a cryostorage device. The object of the invention is also to provide apparatus for implementing the method.

These objects are solved by methods and apparatus of the invention.

SUMMARY OF THE INVENTION

The basic idea of the invention is, in a method for cryostorage especially of biological samples, to transmit data using at least one resonant circuit inductively between at least one data storage which is provided on a sample carrier for receiving at least one sample, and a wireless transmission channel. The combination according to the invention of a data storage for the cryostorage with a resonant circuit advantageously solves the above object by the fact that a plurality of cryostorage devices can be operated simultaneously under cryogenic conditions and the relevant data can be written and/or read without there being a need to provide a special connection of the cryostorage devices to an optical transmission section or bus connection. Data can be transmitted in the cooled state of the sample under conditions identical to the specific storage conditions. Advantageously, the data transmission can take place at temperatures below −40° C. In general, the resonant circuit is formed by an induction element via which the data storage can interact with the electromagnetic transmission channel.

According to a preferred embodiment of the invention the data are transmitted using a transponder which contains the data storage as a transponder storage and the resonant circuit. The inventor has established for the first time that inherently known transponders can surprisingly be used under extreme operating conditions such as during cryopreservation. This particularly applies to operation at a temperature below −60° C. or lower and in cooling containers for holding cooling media. Cooling containers are frequently multi-wall vessels having a complex structure in whose interior at least one transponder system is operated according to the invention. The transponder storage can advantageously take on the function of the data storage for sample data so that the structure of the cryostorage device is simplified.

Particular advantages with regard to a simplified structure are obtained if the data storage, an additional data processing unit and/or another functional element of the cryostorage system can be supplied with energy via the transponder. The functional element can for example be a measuring element or an actuating element for manipulation (processing or treatment) of a cryosample.

According to an advantageous embodiment of the method according to the invention, the resonant circuit is connected via the electromagnetic transmission channel to a transmission antenna from which the data are transmitted to a control and evaluation device. Preferably one transmission antenna is jointly used by a plurality of cryostorage devices according to the invention, whose resonant circuits are tuned to the transmission antenna. In this case, the transmission antenna is advantageously permanently or temporarily arranged in or on an edge of a cooling container to receive a plurality of cryostorage devices.

The data transmitted according to the invention preferably comprise sample data with which the sample is identified and characterised, process data characteristic of the storage conditions of the sample so far, control data with which predetermined operating states of the cryostorage device are adjusted or triggered, and/or additional data such as e.g. personal data and diagnostic results.

The applicability of the invention goes far beyond the conventional identification function of transponders and represents a substantial advantage compared with conventional transponder applications. According to particular embodiments according to the invention, it is even possible to implement control circuits in which the sample data contain measured values which have been obtained on the samples in the cryostorage device and the control data are adjusted using the control and evaluation device depending on the measured values.

A subject of the invention is also a cryostorage device, especially for the storage of biological samples in the frozen state which comprises at least one sample carrier to receive at least one sample and at least one data storage wherein at least one resonant circuit which is provided which is connected to the data storage and is set up to transmit data inductively from the data storage device into a wireless transmission channel and/or conversely.

According to a preferred embodiment of the cryostorage device according to the invention, the resonant circuit is part of a transponder which comprises a data storage and the resonant circuit. The data storage is exclusively a transponder storage as is inherently known from conventional transponders or a data storage which fulfils both functions of a transponder storage and a sample data storage. The data storage can thus advantageously fulfil a plurality of functions. The structure of a cryostorage device is simplified. The data storage can also be integrated in a data processing unit which is respectively allocated to a sample carrier.

A subject of the invention is also a cryostorage system with a plurality of cryostorage devices which each have said structure. The cryostorage system is furthermore equipped with a transmission antenna which is jointly tuned to all cryostorage devices and a control and evaluation device. Data can be transmitted between the control and evaluation device and respectively one data storage via the allocated resonant circuit and the transmission antenna which is connected to the control and evaluation unit in a conducted or wireless fashion. The cryostorage system is preferably arranged in a thermally insulated container to receive a cooling medium, especially liquid nitrogen.

The invention has the following further advantages. The invention is highly adaptable to the specific formulation of the problem. It is possible (i) to uniquely identify the samples (identification) and read out the identification information without contact (read transponders only), (ii) to store the data directly at or on the sample without there being a need for an own conducted power supply at the sample, and (iii) data can be read and written without contact and if necessary under cryogenic conditions (write-read transponder). Furthermore, a non-contact power supply can be provided (passive transponder) for the first time for sensors (measuring device) present on the cryostorage device.

The data transmission and power supply implemented without contact provides new advantages which were not present with earlier applications of transponders. Thus, access to the cryosample with high-frequency electromagnetic fields can be provided through protective packaging (e.g. through foils) and thermal insulation. The non-contact operation prevents any limitation of lifetime by wear, corrosion or contamination. A high failure safety is given so that despite a possibly high number of write and/or read processes on the data storage, longevity of the cryosample in the region of years is guaranteed. Inductive access to sample data is especially possible in the cryopreserved state of the sample.

The non-contact operation also avoids any potential heating effect which could occur as a result of the conducted or optical writing in of information in conventional techniques. The stability of the cryosample is increased.

The invention makes it possible to operate cryostorage systems with a large number of cryostorage devices. Transponders can be used in mass production with high economic efficiency. Transponder systems allow high-grade parallel operation which is especially advantageous for tracking many samples or search functions.

Further advantages and details of the invention can be seen from the description of the appended drawings. In the figures:

DETAILED DESCRIPTION OF THE INVENTION

Figure 1:
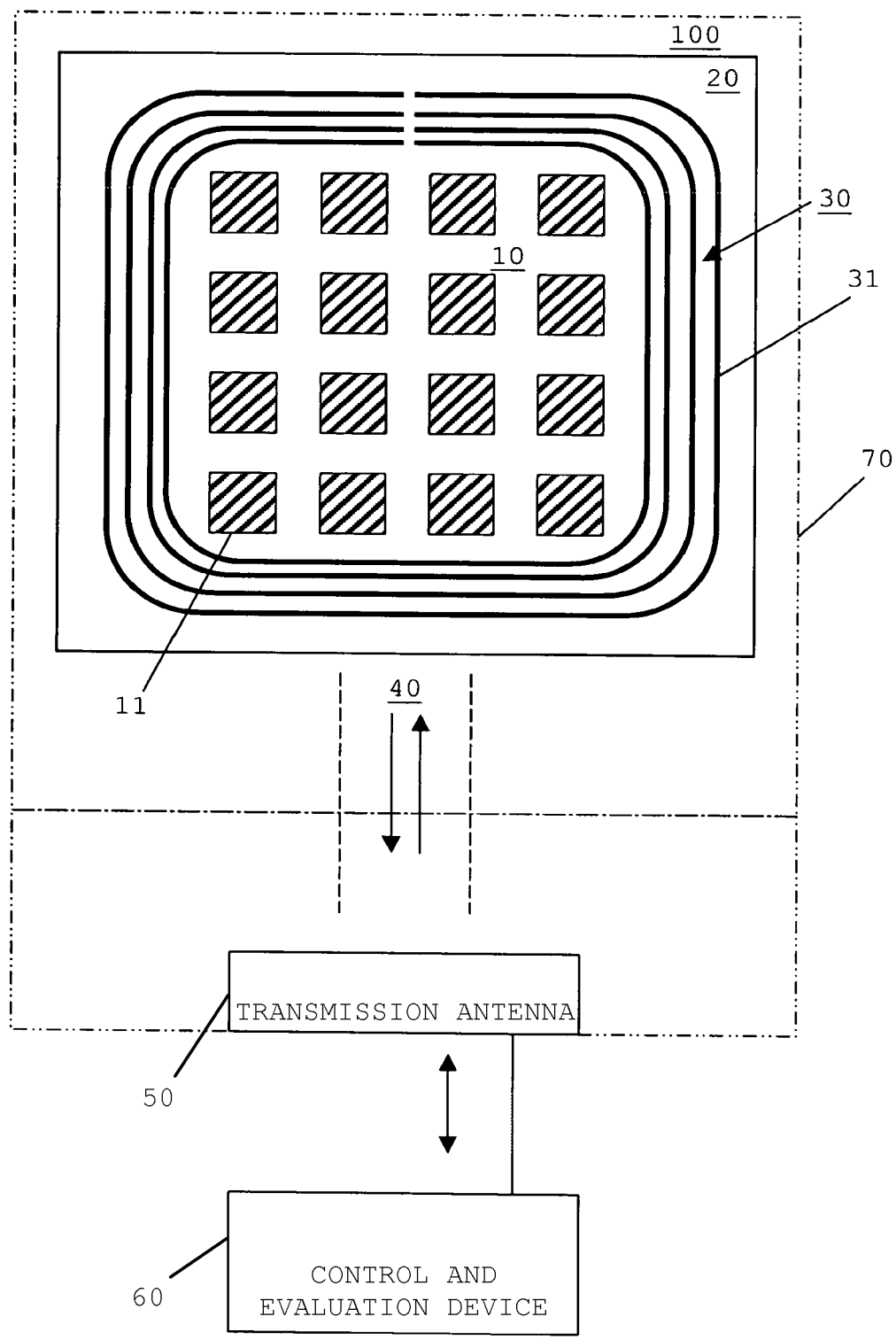
FIG. 1 is a schematic illustration of an embodiment of a cryostorage device according to the invention.

A cryostorage device 100 according to the invention as shown schematically in FIG. 1 comprises a sample carrier 10 to receive at least one sample 11, a data storage 20 and a resonant circuit 30 which is connected to the data storage device 20 and the sample carrier 10. The sample carrier 10 is connected to the data storage 20 as is described for example in the afore-mentioned unpublished patent applications. The samples 11 are preferably formed by biological samples. Preferably provided are miniaturised samples with characteristic volumes in the nl to μl range which respectively contain a sample suspension and biological material such as e.g. cells, cell constituents, macromolecules, micro-organisms, viruses or the like. Reference samples of biological or synthetic origin can also be provided on the sample carrier 10.

The data storage 20 also forms a carrier for the resonant circuit 30 which in the example shown comprises four induction loops 31 which are set up to transmit and/or receive high-frequency electromagnetic oscillations in the kHz range (or higher harmonics thereof). The induction loops 31 are connected to the data storage 20 as is inherently known for conventional transponders.

The at least one resonance frequency range of the resonant circuit 30 forms a transmission channel 40 for high-frequency electromagnetic oscillations for data transmission between the cryostorage device 100 and a transmission antenna 50. The transmission antenna 50 is for its part connected in a conducted or wireless fashion to a control and evaluation device 60 or is integrated therein. The reference number 70 indicates a cryocontainer which contains at least one cryostorage device 100 and a cooling medium and forms a thermal insulation with respect to the surroundings. The transmission antenna 50 can also be arranged in the cryocontainer 70 (see FIG. 3).

The data storage device 20 is for example an EEPROM or a so-called Flash memory which is set up for permanent data storage and is equipped with a microcontroller. The data storage 20 can also be combined with a data processing device. Both components can be provided as a common integrated circuit which is connected to the sample carrier 10.

The induction loops 31 of the resonant circuit 30 are preferably integrated using an inherently known coil-on-chip method as transponder antenna directly on the semiconductor material of the data storage 20 or the encapsulation of a microchip which contains the data storage 20 and possibly a data processing unit. An additional insulation layer can be provided to insulate the resonant circuit 30 with respect to the data storage 20. According to the invention, the sample carrier 10 can also be arranged on an inherently known transponder with the data storage 20 (transponder storage) and the resonant circuit 30. Unlike the diagram in FIG. 1, the samples 11 can also be arranged next to the resonant circuit 30 or on the opposite side of the data storage 20.

Figure 2:
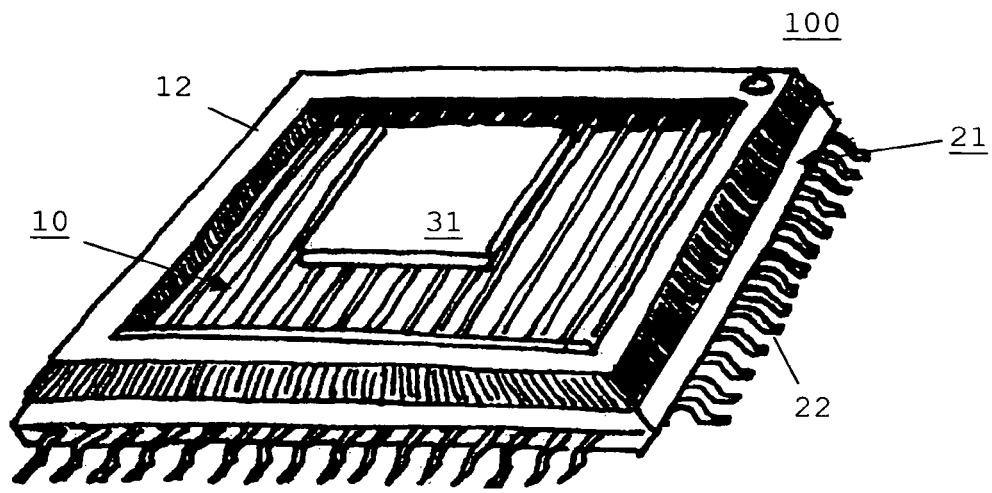
FIG. 2 is another embodiment of a cryostorage device according to the invention.

Further details of a cryostorage device according to the invention are illustrated for example in FIG. 2. In this embodiment the sample carrier 10 comprises hose-shaped chambers to accommodate samples (see DE 101 44 925). The sample chambers are affixed to a frame 12 which is fixed to the encapsulation of an integrated circuit 21 or worked into the encapsulation. The integrated circuit 21 contains a sample data storage. Affixed to the sample chambers is a transponder 32 with the resonant circuit and a data storage. In this arrangement there is no connection between the transponder 32 and the sample data storage. The transponder 32 is used here exclusively to identify the samples. The power and data supply to the circuit 21 is accomplished however via separate connecting leads 22 with which the data storage plugs for example in a holder via which the connection to the control circuit is made. Alternatively an electrical connection can also be formed between the transponder 31 and the circuit 21.

In practical use, the cryostorage devices 100 as shown in FIG. 1 or 2 are used according to the following principles. After loading the sample carrier 10 with biological samples, e.g. cell suspensions, the sample data storage, which is part of the data storage 20, is written with sample data with which the samples are identified and characterised. The sample data, for example, comprise measured values which were determined beforehand for the biological samples as well as information on the origin and properties of the samples. The data can be written in before the cryopreservation via the resonant circuit 30. Alternatively, the data transmission only takes place after the cryopreservation.

In general the cryopreservation comprises transferring the cryostorage device 100 into a reduced-temperature cooling medium such as liquid nitrogen or its vapour. The cryostorage device can also be at least partly in contact with the cooling medium during the sample loading and can have a suitably reduced temperature.

In the cryopreserved state the cryostorage device 100 is stored in the cooling medium. Storage takes place for example in a cooling container 70 (see FIG. 3). During storage further data can be transmitted to the data storage 20. The data comprise, for example process data characteristic of the storage conditions of the sample, further measurement data which were obtained on the donor organism of the preserved samples and/or control data. The process data comprise for example temperature characteristics which were recorded using temperature sensors in the cryocontainer or the surroundings and are stored without contact in the data storage 20. The control data for example contain control information with which predetermined measurement or manipulation processes can be triggered on the sample. For example, in order to determine the storage state of a sample the measurement of a characteristic sample parameter can be carried out externally by means of a start command. The measurement takes place on the cryopreserved sample in the frozen state or alternatively on a locally thawed partial sample. The respective measured values are stored in the data storage 20. In addition to said data transmission to the data storage 20 (writing) at the cryostorage device data transmission, can also take place in the reverse direction to the evaluation and control device 60 (read). The data transmission preferably takes place using transmission protocols such as are inherently known from telemetric applications of transponders. Telemetric transponders are based on data transmission in the form of electrical quantities (e.g. frequency, phase, amplitude) which are in a predetermined relationship with the data to be transmitted.

The write and read processes can advantageously also be integrated in a feedback mechanism. In this mechanism measured values from temperature sensors are initially stored in the data storage 20. The stored data are read out at certain time intervals and used to regulate an external temperature control system. According to the locally prevailing storage conditions the sample is thus actively involved in the cryopreservation process, the cooling and/or the thawing. Conversely, locally determined measured values can be used to control local thawing of samples or sample parts according to predetermined temperature profiles or for treatment or processing of samples, possibly in the locally thawed state.

Changes to the sample carrier 10 can also be brought about with the control data. For example, for removal of part samples control data are sent to predetermined cryostorage devices which bring about a mechanical change on the sample carrier. The mechanical change can for example comprise a thermal separation of part of the sample carrier.

Diagnostic processes on the cryopreserved or locally thawed samples can also be triggered using the control data.

Figure 3:
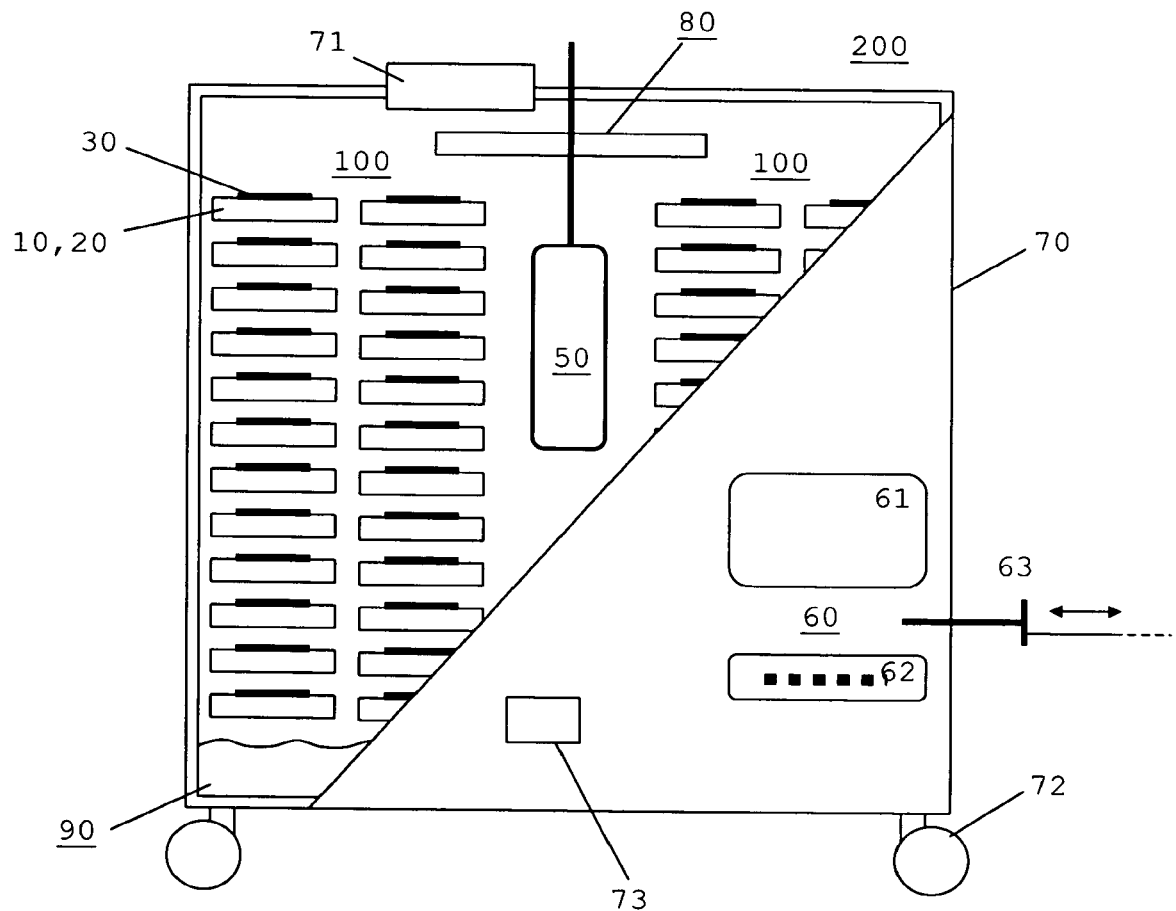
FIG. 3 is a schematic illustration of an embodiment of a cryostorage system according to the invention, with a plurality of cryostorage devices.

FIG. 3 shows a cryostorage system 200 according to the invention with a plurality of cryostorage devices 100 which are formed for example according to the embodiments shown in FIG. 1 or 2. Each cryostorage device 100 comprises a sample carrier 10 with a data storage 20 which is connected to a resonant circuit 30. The cryostorage devices 100 are arranged in the cooling container 70 whose outer wall is only partly shown for reasons of clarity. The cryostorage devices 100 are for example usually inserted in a shelving system with compartments. Access to the cryostorage devices 100 or to samples arranged thereon is made by a lock 71 provided in the container wall. Furthermore, a transmission antenna 50 and a sensor device 80 are provided in the cryocontainer 70. The transmission antenna 50 is connected in a wireless or conducted fashion to the control and evaluation device 60 which is preferably built into the wall of the cooling container 70. The device 60 especially contains a display screen (preferably with a possibility for data entry, for example, a so-called touchscreen screen) and a signal device 62 with which operating states of the cryostorage system 200 can be signalled acoustically or optically. The device 60 also comprises an interface 63 via which a further wireless connection or networking with a central control system is formed.

Cryopreservation using a system from FIG. 3 takes place for example in liquid nitrogen vapour. Liquid nitrogen is poured into the cooling container 70 as cooling medium 90. A schematically illustrated filling device 73 is provided for this. A temperature of around −120° C. to −170° C. forms in the container volume above the cooling medium 90. Alternatively all the cryostorage devices 100 can be inserted in the cooling medium 90.

A particular advantage of the invention is that the cooling system 200 is an independent unit. The cooling container 70 is inherently operational and movable without permanently attached connecting leads. The cooling container 70 can for example be moved on wheels 72.

The features of the invention disclosed in the preceding description, the drawings and the claims can be important both individually and in combination for the implementation of the invention in its various embodiments.

What is claimed is:

1. A method for operating a cryostorage device, which comprises a sample carrier to receive at least one sample and a data storage, said method comprising the step of:
    inductively transmitting data from the data storage into a wireless transmission channel or from the wireless transmission channel to the data storage using a resonant circuit connected to the data storage,
    wherein the step of inductively transmitting data takes place while the at least one sample is in a cryopreserved state at a temperature below −40° C.

2. The method according to claim 1, wherein the data are transmitted using a transponder which comprises the data storage and the resonant circuit.

3. The method according to claim 2, wherein the data storage and/or a data processing unit are supplied with energy using the resonant circuit.

4. The method according to claim 1, wherein the resonant circuit is connected via the wireless transmission channel to a transmission antenna from which the data are transmitted to a control and evaluation device.

5. The method according to claim 1, wherein data are transmitted using the resonant circuit, said data comprising at least one of sample data with which the sample is identified and characterized, process data characteristic of sample storage conditions so far and control data with which predetermined operating states of the cryostorage device are set or triggered.

6. The method according to claim 5, wherein the sample data contain measured values which have been obtained for the samples or the cryostorage device, and the control data are adjusted using the control and evaluation device depending on the measured values.

7. The method according to claim 1, wherein the step of inductively transmitting data takes place at temperatures below −60° C.

8. The method according to claim 1, wherein a telemetric transponder is used for data transmission in a cryostorage device for biological samples.

9. The method according to claim 1, wherein the at least one sample is a biological sample.

* * * * *